United States Patent
Bjorkman et al.

(10) Patent No.: US 9,683,013 B2
(45) Date of Patent: Jun. 20, 2017

(54) AFFINITY CHROMATOGRAPHY MATRIX

(75) Inventors: Tomas Bjorkman, Uppsala (SE); Elin Monie, Uppsala (SE); Gustav Rodrigo, Uppsala (SE)

(73) Assignee: GE HEALTHCARE BIOPROCESS R&D AB, Uppsala (SE)

( * ) Notice: Subject to any disclaimer, the term of this patent is extended or adjusted under 35 U.S.C. 154(b) by 536 days.

(21) Appl. No.: 13/996,023

(22) PCT Filed: Dec. 19, 2011

(86) PCT No.: PCT/SE2011/051536
§ 371 (c)(1),
(2), (4) Date: Jun. 20, 2013

(87) PCT Pub. No.: WO2012/087230
PCT Pub. Date: Jun. 28, 2012

(65) Prior Publication Data
US 2013/0274451 A1    Oct. 17, 2013

Related U.S. Application Data

(60) Provisional application No. 61/424,725, filed on Dec. 20, 2010.

(51) Int. Cl.
| | |
|---|---|
| *B01D 15/38* | (2006.01) |
| *B01J 20/286* | (2006.01) |
| *C07K 1/22* | (2006.01) |
| *B01J 20/289* | (2006.01) |
| *C07K 14/31* | (2006.01) |
| *C07K 14/745* | (2006.01) |
| *B01J 20/32* | (2006.01) |

(52) U.S. Cl.
CPC .......... *C07K 1/22* (2013.01); *B01D 15/3809* (2013.01); *B01J 20/286* (2013.01); *B01J 20/289* (2013.01); *B01J 20/3212* (2013.01); *B01J 20/3219* (2013.01); *B01J 20/3274* (2013.01); *C07K 14/31* (2013.01); *C07K 14/745* (2013.01)

(58) Field of Classification Search
None
See application file for complete search history.

(56) References Cited

U.S. PATENT DOCUMENTS

| | | |
|---|---|---|
| 6,602,977 B1 | 8/2003 | Ljungqvist et al. |
| 2005/0143566 A1 | 6/2005 | Hober |
| 2006/0194950 A1 | 8/2006 | Hober et al. |
| 2006/0194955 A1 | 8/2006 | Hober et al. |
| 2009/0306572 A1* | 12/2009 | Herne .......... C07K 14/31 604/5.01 |

FOREIGN PATENT DOCUMENTS

| | | |
|---|---|---|
| JP | 2010-081866 | 4/2010 |
| WO | WO 2005/003156 | 1/2005 |
| WO | WO 2005/075507 | 8/2005 |
| WO | WO 2006/092338 | 9/2006 |
| WO | WO 2007019376 A2 * | 2/2007 |
| WO | WO 2010/080065 | 7/2010 |

OTHER PUBLICATIONS

Nilsson et al. "a synthetic IgG binding domain based on *Staphylococcal* protein A" Protein Engineering, 1(2), 1987, pp. 107-113.*
Graille, M., et al., PNAS, 97(10), (2000), 5399-5404.
Gulich, S., et al., Journal of Biotechnology, 80, (2000), 169-178.
Kronvall, G., et al., Journal of Molecular Recognition, 12(1), (1999), 38-44.
Cedergren, L., et al., Protein Engineering, 6(4), (1993), 441-448.
Jendeberg et al., "Kinetic Analysis of the Interaction Between Protein A Domain Variants and Human Fc Using Plasmon Resonance Detection," J Molecular Recognition, 8:270-278 (1995).
Hober et al. "Protein A chromatography for antibody purification", J Chromatography B, 848:40-47 (2007).

* cited by examiner

*Primary Examiner* — Daniel E Kolker
*Assistant Examiner* — James Rogers
(74) *Attorney, Agent, or Firm* — Wood IP LLC

(57) ABSTRACT

The present invention relates to a method of separating one or more immunoglobulin containing proteins from a liquid. The method includes first contacting the liquid with a separation matrix comprising ligands immobilized to a support; allowing the immunoglobulin containing proteins to adsorb to the matrix by interaction with the ligands; followed by an optional step of washing the matrix containing the immunoglobulin containing proteins adsorbed thereon; and recovering said immunoglobulin containing proteins by contacting the matrix with an eluent which releases the proteins. The method improves upon previous separation methods in that each of the ligands comprises one or more of a protein A domain (E, D, A, B, C), or protein Z, or a functional variant thereof, with at least one of the monomers having a substitution of the Asparagine at the position corresponding to N28 of B domain of Protein A or Protein Z, and wherein the ligand provides an increase in elution pH compared to non-substituted ligand.

32 Claims, 3 Drawing Sheets

VDAKFDKEQQNAFYEILHLP

NLTEEQRANAFIQSLKDDPSQ

SANLLAEAKKLNDAQAPK

Figure 1

Protein A (five domains, EDABC)

```
(N-terminus)  < Helix 1 >      < Helix 2 >       < Helix 3 >
              QQNAFYQVLNMPNLNADQRNGFIQSLKDDPSQSANVLGEAQKLNDSQAPK    (E)  SEQ IN No: 4
ADAQQNNFNKDQQSAFYEILNMPNLNEAQRNGFIQSLKDDPSQSTNVLGEAKKLNESQAPK    (D)  SEQ IN No: 5
ADNNFNKEQQNAFYEILNMPNLNEEQRNGFIQSLKDDPSQSANLLSEAKKLNESQAPK       (A)  SEQ IN No: 6
ADNKFNKEQQNAFYEILHLPNLNEEQRNGFIQSLKDDPSQSANLLAEAKKLNDAQAPK       (B)  SEQ IN No: 7
ADNKFNKEQQNAFYEILHLPNLTEEQRNGFIQSLKDDPSVSKEILAEAKKLNDAQAPK       (C)  SEQ IN No: 8
                                                                 (C-terminus)
```

Figure 2

AQVDAKFDKE QQNAFYEILH LPNLTEEQRA AFIQSLKDDP SQSANLLAEA
KKLNDAQAPK VDAKFDKEQQ NAFYEILHLP NLTEEQRAAF IQSLKDDPSQ
SANLLAEAKK LNDAQAPKC

Figure 3

SEQUENCE LISTING

<160> NUMBER OF SEQ ID NOS: 21

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Escherichia coli

<400> SEQUENCE: 2

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 3
<211> LENGTH: 119
<212> TYPE: PRT
<213> ORGANISM: Escherichia coli

<400> SEQUENCE: 3

Ala Gln Val Asp Ala Lys Phe Asp Lys Glu Gln Gln Asn Ala Phe Tyr
1               5                   10                  15

Glu Ile Leu His Leu Pro Asn Leu Thr Glu Glu Gln Arg Ala Ala Phe
            20                  25                  30

Ile Gln Ser Leu Lys Asp Asp Pro Ser Gln Ser Ala Asn Leu Leu Ala
        35                  40                  45

Glu Ala Lys Lys Leu Asn Asp Ala Gln Ala Pro Lys Val Asp Ala Lys
    50                  55                  60

Phe Asp Lys Glu Gln Gln Asn Ala Phe Tyr Glu Ile Leu His Leu Pro
65                  70                  75                  80

Asn Leu Thr Glu Glu Gln Arg Ala Ala Phe Ile Gln Ser Leu Lys Asp
            85                  90                  95

Asp Pro Ser Gln Ser Ala Asn Leu Leu Ala Glu Ala Lys Lys Leu Asn
        100                 105                 110

Asp Ala Gln Ala Pro Lys Cys
    115

<210> SEQ ID NO 4
<211> LENGTH: 50
<212> TYPE: PRT
<213> ORGANISM: Staphylococcus aureus

<400> SEQUENCE: 4

Gln Gln Asn Ala Phe Tyr Gln Val Leu Asn Met Pro Asn Leu Asn Ala
1               5                   10                  15

Asp Gln Arg Asn Gly Phe Ile Gln Ser Leu Lys Asp Asp Pro Ser Gln
            20                  25                  30

Ser Ala Asn Val Leu Gly Glu Ala Gln Lys Leu Asn Asp Ser Gln Ala
        35                  40                  45

Pro Lys
    50

<210> SEQ ID NO 5
<211> LENGTH: 61
<212> TYPE: PRT
<213> ORGANISM: Staphylococcus aureus

<400> SEQUENCE: 5

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 6
<211> LENGTH: 58
<212> TYPE: PRT
<213> ORGANISM: Staphylococcus aureus

<400> SEQUENCE: 6

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55

<210> SEQ ID NO 7
<211> LENGTH: 58
<212> TYPE: PRT
<213> ORGANISM: Staphylococcus aureus

<400> SEQUENCE: 7

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT

<213> ORGANISM: Staphylococcus aureus

<400> SEQUENCE: 8

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 9
<211> LENGTH: 58
<212> TYPE: PRT
<213> ORGANISM: Escherichia coli
<220> FEATURE:
<221> NAME/KEY: misc_feature
<222> LOCATION: (28)..(28)
<223> OTHER INFORMATION: Xaa can be any naturally occurring amino acid

<400> SEQUENCE: 9

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Xaa Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 10
<211> LENGTH: 119
<212> TYPE: PRT
<213> ORGANISM: Escherichia coli
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid

<400> SEQUENCE: 10

Ala Gln Val Asp Ala Lys Phe Asp Lys Glu Gln Gln Asn Ala Phe Tyr
1               5                   10                  15

Glu Ile Leu His Leu Pro Asn Leu Thr Glu Glu Gln Arg Xaa Ala Phe
            20                  25                  30

Ile Gln Ser Leu Lys Asp Asp Pro Ser Gln Ser Ala Asn Leu Leu Ala
        35                  40                  45

Glu Ala Lys Lys Leu Asn Asp Ala Gln Ala Pro Lys Val Asp Ala Lys
    50                  55                  60

Phe Asp Lys Glu Gln Gln Asn Ala Phe Tyr Glu Ile Leu His Leu Pro
65                  70                  75                  80

Asn Leu Thr Glu Glu Gln Arg Xaa Ala Phe Ile Gln Ser Leu Lys Asp
                85                  90                  95

Asp Pro Ser Gln Ser Ala Asn Leu Leu Ala Glu Ala Lys Lys Leu Asn
            100                 105                 110

Asp Ala Gln Ala Pro Lys Cys
        115

<210> SEQ ID NO 11
<211> LENGTH: 58
<212> TYPE: PRT
<213> ORGANISM: Escherichia coli

<400> SEQUENCE: 11

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Ala Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 12
<211> LENGTH: 58
<212> TYPE: PRT
<213> ORGANISM: Escherichia coli
<220> FEATURE:
<221> NAME/KEY: misc_feature
<222> LOCATION: (28)..(28)
<223> OTHER INFORMATION: Xaa can be any naturally occurring amino acid

<400> SEQUENCE: 12

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Xaa Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 13
<211> LENGTH: 58
<212> TYPE: PRT
<213> ORGANISM: Escherichia coli

<400> SEQUENCE: 13

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Ala Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 14
<211> LENGTH: 58
<212> TYPE: PRT
<213> ORGANISM: Escherichia coli
<220> FEATURE:
<221> NAME/KEY: misc_feature
<222> LOCATION: (28)..(28)
<223> OTHER INFORMATION: Xaa can be any naturally occurring amino acid

<400> SEQUENCE: 14

Ala Asp Asn Asn Phe Asn Lys Glu Gln Gln Asn Ala Phe Tyr Glu Ile
1               5                   10                  15

```
Leu Asn Met Pro Asn Leu Asn Glu Glu Gln Arg Xaa Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55
```

<210> SEQ ID NO 15
<211> LENGTH: 58
<212> TYPE: PRT
<213> ORGANISM: Escherichia coli

<400> SEQUENCE: 15

```
Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Ala Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55
```

<210> SEQ ID NO 16
<211> LENGTH: 58
<212> TYPE: PRT
<213> ORGANISM: Escherichia coli
<220> FEATURE:
<221> NAME/KEY: misc_feature
<222> LOCATION: (28)..(28)
<223> OTHER INFORMATION: Xaa can be any naturally occurring amino acid

<400> SEQUENCE: 16

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Xaa Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 17
<211> LENGTH: 58
<212> TYPE: PRT
<213> ORGANISM: Escherichia coli

<400> SEQUENCE: 17

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Ala Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 18
<211> LENGTH: 50
<212> TYPE: PRT
<213> ORGANISM: Escherichia coli

```
<220> FEATURE:
<221> NAME/KEY: misc_feature
<222> LOCATION: (20)..(20)
<223> OTHER INFORMATION: Xaa can be any naturally occurring amino acid

<400> SEQUENCE: 18

Gln Gln Asn Ala Phe Tyr Gln Val Leu Asn Met Pro Asn Leu Asn Ala
1               5                   10                  15

Asp Gln Arg Xaa Gly Phe Ile Gln Ser Leu Lys Asp Asp Pro Ser Gln
            20                  25                  30

Ser Ala Asn Val Leu Gly Glu Ala Gln Lys Leu Asn Asp Ser Gln Ala
        35                  40                  45

Pro Lys
    50

<210> SEQ ID NO 19
<211> LENGTH: 50
<212> TYPE: PRT
<213> ORGANISM: Escherichia coli

<400> SEQUENCE: 19

Gln Gln Asn Ala Phe Tyr Gln Val Leu Asn Met Pro Asn Leu Asn Ala
1               5                   10                  15

Asp Gln Arg Ala Gly Phe Ile Gln Ser Leu Lys Asp Asp Pro Ser Gln
            20                  25                  30

Ser Ala Asn Val Leu Gly Glu Ala Gln Lys Leu Asn Asp Ser Gln Ala
        35                  40                  45

Pro Lys
    50

<210> SEQ ID NO 20
<211> LENGTH: 61
<212> TYPE: PRT
<213> ORGANISM: Escherichia coli
<220> FEATURE:
<221> NAME/KEY: misc_feature
<222> LOCATION: (31)..(31)
<223> OTHER INFORMATION: Xaa can be any naturally occurring amino acid

<400> SEQUENCE: 20

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Xaa Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 21
<211> LENGTH: 61
<212> TYPE: PRT
<213> ORGANISM: Escherichia coli

<400> SEQUENCE: 21

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Ala Gly
            20                  25                  30

Phe Ile Gln Ser Leu Lys Asp Asp Pro Ser Gln Ser Thr Asn Val Leu
        35                  40                  45
```

```
Gly Glu Ala Lys Lys Leu Asn Glu Ser Gln Ala Pro Lys
 50                  55                  60
```

AFFINITY CHROMATOGRAPHY MATRIX

STATEMENT REGARDING SEQUENCE LISTING

The Sequence Listing associated with this application is part of the description and is provided in text the form of an Annex C/ST.25 text file in lieu of a paper copy, and is hereby incorporated by reference into the specification. The name of the text file containing the Sequence Listing is 249970-7_SequenceListing.txt. The text file is 12 kb, was created on 13 Jan. 2017, and is being submitted electronically via EFS-Web.

CROSS-REFERENCE TO RELATED APPLICATIONS

This application is a filing under 35 U.S.C. 371 of international application number PCT/SE2011/051536, filed Dec. 19, 2011, published on Jun. 28, 2012 as WO 2012/087230, which claims priority to U.S. provisional patent application No. 61/424,725 filed Dec. 20, 2010.

FIELD OF THE INVENTION

The present invention relates to the field of affinity chromatography, and more specifically to separation matrix containing ligand containing one or more of a protein A domain (E, D, A, B, C), or protein Z, wherein in at least one of the domains (monomers), the Asparagine at the position corresponding to N28 of B domain of Protein A or Protein Z has been substituted with another amino acid. The invention also relates to methods for the separation of proteins of interest with aforementioned matrix, with the advantage of increased elution pH.

BACKGROUND OF THE INVENTION

Immunoglobulins represent the most prevalent biopharmaceutical products in either manufacture or development worldwide. The high commercial demand for and hence value of this particular therapeutic market has lead to the emphasis being placed on pharmaceutical companies to maximise the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection. At present, SpA-based affinity medium probably is the most widely used affinity medium for isolation of monoclonal antibodies and their fragments from different samples including industrial feed stocks from cell cultures. Accordingly, various matrices comprising protein A ligands are commercially available, for example, in the form of native protein A (e.g. Protein A SEPHAROSE™, GE Healthcare, Uppsala, Sweden) and also comprised of recombinant protein A (e.g. rProtein A SEPHAROSE™, GE Healthcare). More specifically, the genetic manipulation performed in the commercial recombinant protein A product is aimed at facilitating the attachment thereof to a support.

These applications, like other affinity chromatography applications, require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitising agent is NaOH, and the concentration thereof can range from 0.1 up to e.g. 1 M, depending on the degree and nature of contamination. This strategy is associated with exposing the matrix for pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focussed on the development of engineered protein ligands that exhibit an improved capacity to withstand alkaline pH-values. For example, Gülich et al (Journal of Biotechnology 80 (2000), 169-178) suggested protein engineering to improve the stability properties of a Streptococcal albumin-binding domain (ABD) in alkaline environments. Gülich et al created a mutant of ABD, wherein all the four aspargine residues have been replaced by leucine (one residue), asparte (two residues) and lysine (one residue). Further, Gülich et al report that their mutant exhibits a target protein binding behaviour similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Recent work show that changes can also be made to protein A (SpA) to effect similar properties. US patent application 2005/0143566 discloses that when at least one asparagine residue is mutated to an amino acid other than glutamine or aspartic acid, the mutation confers an increased chemical stability at pH-values of up to about 13-14 compared to the parental SpA, such as the B-domain of SpA, or Protein Z, a synthetic construct derived from the B-domain of SpA (U.S. Pat. No. 5,143,844). The authors show that when these mutated proteins are used as affinity ligands, the separation media as expected can better withstand cleaning procedures using alkaline agents. US patent application 2006/0194955 shows that the mutated ligands can better withstand proteases thus reducing ligand leakage in the separation process. Another application, US patent application 2006/0194950 shows that the alkali stable SpA domains can be further modified such that the ligands lacks affinity for Fab but retains Fc affinity, for example by a G29A mutation.

Historically the native protein A containing 5 IgG binding domains was used for production of all protein A affinity media. Using recomenband technology a number of protein A construct have been produced all containing 4 or 5 IgG binding domains. A recent study shows that dimeric ligands have a similar, or increased binding capacity compared to tetrameric ligands (WO 2010/080065).

It is well known that some antibodies are prone to aggregation or sensitive (e.g. they can lose activity) at low pH. There is still a need in this field to obtain a separation matrix containing protein ligands having an increased elution pH for antibody or related targets.

BRIEF SUMMARY OF THE INVENTION

One object of the present invention is to provide an affinity separation matrix, which comprises protein ligands capable of binding immunoglobulins, such as IgG, IgA and/or IgM, preferably via their Fc-fragments. These ligands carry a substitution of the Asparagine at the position corresponding to N28 of B domain of Protein A or Protein Z, in at least one of the monomeric domains of protein A (E, D, A, B, C) or protein Z, thus have a higher elution pH, as compared to ligands without the substitution. Preferably, the ligands are multimeric, i.e., containing more than one monomeric domains selected from protein A (E, D, A, B, C) and protein Z.

Another object of the invention is to provide a method for separating one or more immunoglobulin containing proteins, using the current affinity matrix. By using affinity ligands with the substitution, the method unexpectedly achieves increased elution pH for the target molecules.

Thus the invention provides a method for either producing a purified product, such as a pure immunoglobulin fraction or alternatively a liquid from which the immunoglobulin has been removed, or to detect the presence of immunoglobulin in a sample. The ligands according to the invention exhibit an increased elution pH, which renders the ligands attractive candidates for cost-effective large-scale operation.

One or more of the above-defined objects can be achieved as described in the appended claims.

BRIEF DESCRIPTION OF THE DRAWINGS

FIG. 1 shows the amino acid sequence (SEQ ID NO:2) of protein Z, with the Asparagine at position 28 shown in bold having the mutations N3A, N6D, and N23T.

FIG. 2 shows an alignment of the amino acid sequences from each of the five domains of protein A, with the Asparagine at the position corresponding to N28 of B domain of Protein A in bold. Also shown are the location of the three alpha-helices (Graille et al, PNAS 2000, 97 (10): 5399-5404; Deisenhofer, Biochemistry 1981, 20 (9): 2361-2370).

FIG. 3 shows the amino acid sequence (SEQ ID NO:3) of a dimeric ligand, used in the experimental studies, with two copies of protein Z, each with an N28A substitution and having the mutations N3A, N6D, and N23T.

DETAILED DESCRIPTION OF THE INVENTION

Definitions

The term "protein" is used herein to describe proteins as well as fragments thereof. Thus, any chain of amino acids that exhibits a three dimensional structure is included in the term "protein", and protein fragments are accordingly embraced.

The term "functional variant" of a protein means herein a variant protein, wherein the function, in relation to the invention defined as affinity and stability, are essentially retained. Thus, one or more amino acids that are not relevant for said function may have been exchanged.

The term "parental molecule" is used herein for the corresponding protein in the form before a mutation according to the invention has been introduced.

The term "structural stability" refers to the integrity of three-dimensional form of a molecule, while "chemical stability" refers to the ability to withstand chemical degradation.

The term "Fc fragment-binding" protein means that the protein is capable of binding to the Fc fragment of an immunoglobulin. However, it is not excluded that an Fc fragment-binding protein also can bind other regions, such as Fab regions of immunoglobulins.

In the present specification, if not referred to by their full names, amino acids are denoted with the conventional one-letter or three letter symbols.

Mutations are defined herein by the number of the position exchanged, preceded by the wild type or non-mutated amino acid and followed by the mutated amino acid. Thus, for example, the mutation of an asparagine in position 23 to a threonine is denoted N23T.

The present invention in one aspect relates to a method of separating one or more immunoglobulin containing proteins from a liquid, which method comprises (a) contacting the liquid with a separation matrix comprising ligands immobilised to a support; (b) allowing the immunoglobulin containing proteins to adsorb to the matrix by interaction with the ligands; (c) an optional step of washing the adsorbed immunoglobulin containing proteins; and (d) recovering the immunoglobulin containing proteins by contacting the matrix with an eluent which releases the proteins. The method provides increased elution pH for the immunoglobulin molecules by using a ligand, each comprises one or more domains (i.e., monomers) of staphylococcal Protein A (SpA) (E, D, A, B, C) or protein Z or a functional variant thereof, wherein the Asparagine at the position corresponding to N28 of B domain of Protein A or Protein Z has been substituted with any other amino acid.

The immunoglobulin-binding protein (i.e., ligand) can be any protein with a native immunoglobulin-binding capability, such as Staphylococcal protein A (SpA) or Streptococcal protein G (SpG), or recombinant proteins containing IgG-binding domains of these proteins. For a review of other such proteins, see e.g. Kronvall, G., Jonsson, K. Receptins: a novel term for an expanding spectrum of natural and engineered microbial proteins with binding properties for mammalian proteins, J. Mol. Recognit. 1999 January-February; 12(1):38-44. The ligands can comprise one of more of the E, D, A, B and C domains of SpA. More preferably the ligands comprise domain B of protein A, domain C of protein A or the engineered protein Z.

Every protein Z or protein A domain contains an Asparagine at the position corresponding to N28 of B domain of Protein A or Protein Z (see e.g., FIG. 1, FIG. 2, and SEQ ID NO: 1-8).

As shown in FIG. 2, the sequences among the five domains of Protein A are highly related. There are no deletions or insertion, and many of the substitutions are conservative changes with minimal potential change to the structure or function of the protein. For example, there are only four changes between the B domain and the C domain, over the entire 58 amino acid polypeptide. Thus, the Asparagine at the position corresponding to N28 of B domain of Protein A or Protein Z in each of these domains have a similar structural/functional contribution to protein A or ligand containing the domain. Similarly, substitution of the Asparagine causes a similar effect to the structure/function of the ligand containing such a change.

In certain embodiments, the Asparagine is substituted with an amino acid that increases the elution pH while maintaining the binding capacity to IgG. Preferably, the Asparagine is substituted for an amino acid such as, e.g. Glu, Leu, Gln, Trp, Lys, Asp or Arg. More preferably, the substitution is to an Alanine. Specifically, protein Z (SEQ ID NO: 2) with N28 substituted with another amino acid X has a sequence of SEQ ID NO.: 9. Dimeric protein Z with N28 substituted with another amino acid X in each protein Z monomer has a sequence of SEQ ID NO.: 10. Protein Z (SEQ ID NO: 2) with N28A substitution has a sequence of SEQ ID NO.: 11. Domain B (SEQ ID NO: 1) with a N28 substituted with another amino acid X has a sequence of SEQ ID NO: 12. Domain B (SEQ ID NO: 1) with a N28A substitution has a sequence of SEQ ID NO: 13. Domain A (SEQ ID NO: 6) with a N28 substituted with another amino acid X has a sequence of SEQ ID NO: 14. Domain A (SEQ ID NO: 6) with a N28A substitution has a sequence of SEQ ID NO: 15. Domain C (SEQ ID NO: 8) with a N28 substituted with another amino acid X has a sequence of SEQ ID NO: 16. Domain C (SEQ ID NO: 8) with a N28A substitution has a sequence of SEQ ID NO: 17, Domain E (SEQ ID NO: 4) with the position corresponding to N28 of B domain of Protein A substituted with another amino acid X has a sequence of SEQ ID NO: 18. Domain E (SEQ ID NO: 4) with the position corresponding to N28 of B domain of Protein A substituted with alanine has a sequence of SEQ ID NO: 19. Domain D (SEQ ID NO: 5) with the position corresponding to N28 of B domain of Protein A substituted with another amino acid X has a sequence of SEQ ID NO: 20. Domain E (SEQ ID NO: 4) with the position corresponding to N28 of B domain of Protein A substituted with alanine has a sequence of SEQ ID NO: 21. In some embodiments, X is Ala, Glu, Leu, Gln, Trp, Lys, Asp or Arg.

In certain preferred embodiments, the parental molecular sequence comprises the sequences defined by SEQ ID NO: 1-2, 4-8, or any functional variance thereof.

In certain embodiments, the Asparagine at the position corresponding to N28 of B domain of Protein A or Protein Z in at least one of the monomeric domains in a multimeric ligand are substituted. In other embodiments, the Asparagine residue in all the monomeric domains in a multimeric ligand are substituted.

The substitution of the Asparagine residue at the position corresponding to N28 of B domain of Protein A or Protein Z unexpectedly increases the elution pH of immunoglobulins, such as IgG, IgA and/or IgM, or fusion proteins containing an Fc-fragment. Preferably, the elution pH increases by between 0.2 to over 1.0 pH. More preferably, the elution pH increases at least 0.3 pH, most preferably, the elution pH increases at least 0.4 pH. Alternatively, the elution pH is increased to >4.0, preferably pH>4.2, while the recovery yield is at least 80% or even >90% of that of the parental ligands.

In one embodiment, the ligands are also rendered alkali-stable, such as by mutating at least one other Asparagine residue of at least one of the monomeric domains of the SpA domain B or protein Z to an amino acid other than glutamine. As discussed earlier, US patent application 2005/ 0143566 discloses that when at least one asparagine residue is mutated to an amino acid other than glutamine or aspartic acid, the mutation confers the ligand an increased chemical stability at high pH (e.g., N23T). Further, affinity media including these ligands can better withstand cleaning procedures using alkaline agents. US patent application 2006/ 0194955 shows that the mutated ligands can also better withstand proteases thus reducing ligand leakage in the separation process. The disclosures of these applications are hereby incorporated by reference in their entirety.

In another embodiment, the ligand(s) so prepared lack any substantial affinity for the Fab part of an antibody, while having affinity for the Fc part. Thus, in certain embodiments, at least one glycine of the ligands has been replaced by an alanine. US patent application 2006/0194950 shows that the alkali stable domains can be further modified such that the ligands lacks affinity for Fab but retains Fc affinity, for example by a G29A mutation. The disclosure of the application is hereby incorporated by reference in its entirety. The numbering used herein of the amino acids is the conventionally used in this field, exemplified by the position on domain B of protein A, and the skilled person in this field can easily recognize the position to be mutated for each domain of E, D, A, B, C.

In an advantageous embodiment, the ligand is made of multimer copies of domain B, and the alkali-stability of domain B has been achieved by mutating at least one other asparagine residue to an amino acid other than glutamine (e.g. N23T); and contains a mutation of the amino acid residue at position 29 of the alkali-stable domain B, such as a G29A mutation.

In an advantageous embodiment, the ligand is made of multimer copies of domain C, with the Arginine residue at N28 mutated, or functional variants thereof. Optionally, the ligand also contains a mutation of the amino acid residue at position 29, such as a G29A mutation.

In another embodiment, the ligand is made of multimer copies of protein Z in which the alkali-stability has been achieved by mutating at least one asparagine residue to an amino acid other than glutamine. In an advantageous embodiment, the alkali-stability has been achieved by mutating at least the asparagine residue at position 23 to an amino acid other than glutamine.

As the skilled person in this field will easily understand, the substitution of Asparagine at position 28, the mutations to provide alkaline-stability, and the G to A mutation may be carried out in any order of sequence using conventional molecular biology techniques. Further, the ligands can be expressed by a vector containing a nucleic acid sequence encoding the mutated protein ligands. Alternatively, they can also be made by protein synthesis techniques. Methods for synthesizing peptides and proteins of predetermined sequences are well known and commonly available in this field.

Thus, in the present invention, the term "alkali-stable domain B of Staphylococcal Protein A" means an alkali-stabilized protein based on Domain B of SpA, such as the mutant protein described in US patent application 2005/ 0143566 and US patent application 2006/0194950; as well as other alkali-stable proteins of other origin but having a functionally equivalent amino acid sequence.

As the skilled person will understand, the expressed protein should be purified to an appropriate extent before been immobilized to a support. Such purification methods are well known in the field, and the immobilization of protein-based ligands to supports is easily carried out using standard methods. Suitable methods and supports will be discussed below in more detail.

Accordingly, in one embodiment, a mutated protein according to the invention comprises at least about 75%, such as at least about 80% or preferably at least about 95%, of the sequence as defined in SEQ ID NO: 1 or 2, with the proviso that an asparagine mutation is not in position 21.

In the present specification, SEQ ID NO: 1 defines the amino acid sequence of the B-domain of SpA:

Ala Asp Asn Lys Phe Asn Lys Glu Gln Gln Asn Ala

Phe Tyr Glu Ile Leu His Leu Pro Asn Leu Asn Glu

Glu Gln Arg Asn Gly Phe Ile Gln Ser Leu Lys Asp

Asp Pro Ser Gln Ser Ala Asn Leu Leu Ala Glu Ala

Lys Lys Leu Asn Asp Ala Gln Ala Pro Lys

SEQ ID NO: 2 defines a protein known as protein Z:

Val Asp Asn Lys Phe Asn Lys Glu Gln Gln Asn Ala

Phe Tyr Glu Ile Leu His Leu Pro Asn Leu Asn Glu

Glu Gln Arg Asn Ala Phe Ile Gln Ser Leu Lys Asp

Asp Pro Ser Gln Ser Ala Asn Leu Leu Ala Glu Ala

Lys Lys Leu Asn Asp Ala Gln Ala Pro Lys

Protein Z is a synthetic construct derived from the B-domain of SpA, wherein the glycine in position 29 has been exchanged for alanine, see e.g. Ståhl et al, 1999: Affinity fusions in biotechnology: focus on protein A and protein G, in The Encyclopedia of Bioprocess Technology: Fermentation, Biocatalysis and Bioseparation. M. C. Fleckinger and S. W. Drew, editors. John Wiley and Sons Inc., New York, 8-22.

In one embodiment, the above described mutant protein is comprised of the amino acid sequence defined in SEQ ID NO: 1-2 or 4-8, or is a functional variant thereof, with a substitution of Asparagine at the position corresponding to N28 of B domain of Protein A. The term "functional variant" as used in this context includes any similar sequence, which comprises one or more further variations in amino acid positions that have no influence on the mutant protein's affinity to immunoglobulins or its improved chemical stability in environments of increased pH-values.

In an advantageous embodiment, the present substitutions of Asparagine are selected from the group that consists of amino acids of, e.g. Glu, Leu, Gln, Trp, Lys, Asp and Arg; and wherein the parental molecule comprises the sequence defined by SEQ ID NO: 1-2 and 4-8, or any functional variance thereof. More preferably, the substitution is to an Alanine. As mentioned above, in order to achieve a mutant protein useful as a ligand with high binding capacity for a prolonged period of time in alkaline conditions, mutation of the asparagine residue in position 21 is avoided. In one embodiment, the asparagine residue in position 3 is not mutated.

The substitution of the Asparagine residue at the position corresponding to N28 of B domain of Protein A or Protein Z unexpectedly increases the elution pH of immunoglobulins, such as IgG, IgA and/or IgM, or fusion proteins containing an Fc-fragment. Preferably, the elution pH increases by between 0.2 to over 1.0 pH. More preferably, the elution pH increases at least 0.3 pH, most preferably, the elution pH increases at least 0.4 pH. Alternatively, the elution pH is increased to >4.0, preferably pH>4.2, while the recovery yield is at least 80% or even >90% of that of the parental ligands.

In certain embodiments, the Asparagine residue in at least one of the monomers in a multimeric ligand are substituted. In other embodiments, the Asparagine residue in all the monomers in a multimeric ligand are substituted.

In one advantageous embodiment, an asparagine residue located between a leucine residue and a glutamine residue has also been mutated, for example to a threonine residue. Thus, in one embodiment, the asparagine residue in position 23 of the sequence defined in SEQ ID NO: 2 has been mutated, for example to a threonine residue. In a specific embodiment, the asparagine residue in position 43 of the sequence defined in SEQ ID NO: 2 has also been mutated, for example to a glutamic acid. In the embodiments where amino acid number 43 has been mutated, it appears to most advantageously be combined with at least one further mutation, such as N23T.

Thus, the invention encompasses the above-discussed monomeric mutant proteins. However, such protein monomers can be combined into multimeric ligands, such as dimers, trimers, tetramers, pentamers, hexamers etc. Accordingly, another aspect of the present invention is a multimer comprised of at least one of the mutated proteins according to the invention together with one or more further units, preferably also mutant proteins according to the invention. Thus, the present invention is e.g. a dimer comprised of two repetitive units, or a tetramer comprised of four repetitive units.

In certain embodiments, the multimeric ligands contain two or more copies of the same monomeric domain from domain E, D, A, B, C of protein A, or protein Z, or any functional variants.

In other embodiments, the multimeric ligands contain two or more different monomeric domains selected from domain E, D, A, B, C of protein A, or protein Z, or any functional variants.

In one embodiment, the multimer according to the invention comprises monomer units linked by a stretch of amino acids preferably ranging from 0 to 15 amino acids, such as 0-10 or 5-10 amino acids. The nature of such a link should preferably not destabilize the spatial conformation of the protein units. Furthermore, said link should preferably also be sufficiently stable in alkaline environments not to impair the properties of the mutated protein units.

In another embodiment, the present dimeric ligands comprise the sequence of SEQ ID NO: 3:

AQVDAKFDKE QQNAFYEILH LPNLTEEQRA AFIQSLKDDP

SQSANLLAEA KKLNDAQAPK VDAKFDKEQQ NAFYEILHLP

NLTEEQRAAF IQSLKDDPSQ SANLLAEAKK LNDAQAPKC

The current invention unexpectedly found that when comparing the elution pH of the ligands, a substitution of the Asparagine at the position corresponding to N28 of B domain of Protein A or Protein Z in at least one of the monomeric domains of the ligand provides a higher elution pH compared to non-substituted ligands.

In one embodiment, the invention relates to a matrix for affinity separation, which matrix comprises ligands that comprise immunoglobulin-binding protein coupled to a solid support. Preferably, the Asparagine at the position corresponding to N28 of B domain of Protein A or Protein Z, in at least one of the monomeric domains of protein A (domain E, D, A, B, C) or protein Z, has been substituted to another amino acid. Preferably, the ligands are multimeric, i.e., containing more than one monomeric domains selected from protein A (domain E, D, A, B, C) and protein Z. The present matrix, when compared to a matrix without the substitution, exhibits an increased elution pH. The mutated protein ligand is preferably an Fc-fragment-binding protein, and can be used for selective binding of IgG, IgA and/or IgM, preferably IgG.

The matrix according to the invention can comprise the mutant protein as described above in any embodiment thereof as ligand. In the most preferred embodiment, the ligands present on the solid support comprise a substitution as described above.

The solid support of the matrix according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—$CONH_2$, possibly in N— substituted forms), amino (—$NH_2$, possibly in substituted form), oligo- or polyethylenoxy groups on their external and, if present, also on internal surfaces. In one embodiment, the polymers may, for instance, be based on polysaccharides, such as dextran, starch, cellulose, pullulan, agar, agarose etc, which advantageously have been cross-linked, for instance with bisepoxides, epihalohydrins, 1,2,3-trihalo substituted lower hydrocarbons, to provide a suitable porosity and rigidity. In the most preferred embodiment, the solid support is porous agarose beads, which can be crosslinked. The supports used in the present invention can easily be prepared according to standard methods, such as inverse suspension gelation (S Hjertén: Biochim Biophys Acta 79(2), 393-398 (1964). Alternatively, the base matrices are commercially available products, such as SEPHAROSE™ FF (GE Healthcare). In an embodiment, which is especially advantageous for large-scale separations, the support has been adapted to increase its rigidity, and hence renders the matrix more suitable for high flow rates.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used.

In another alternative, the solid support according to the invention comprises a support of inorganic nature, e.g. silica, zirconium oxide etc.

In yet another embodiment, the solid support is in another form such as a surface, a chip, capillaries, or a filter.

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batchwise mode will be used.

The ligand may be attached to the support via conventional coupling techniques utilising, e.g. amino and/or carboxy groups present in the ligand. Bisepoxides, epichlorohydrin, CNBr, N-hydroxysuccinimide (NHS) etc are well-known coupling reagents. Between the support and the ligand, a molecule known as a spacer can be introduced, which improves the availability of the ligand and facilitates the chemical coupling of the ligand to the support. Alternatively, the ligand may be attached to the support by non-covalent bonding, such as physical adsorption or biospecific adsorption. The ligand content of the matrix may e.g. be 5-15 mg/ml matrix and can advantageously be 5-10 mg/ml.

In an advantageous embodiment, the present ligand has been coupled to the support by thioether bonds. Methods for performing such coupling are well-known in this field and easily performed by the skilled person in this field using standard techniques and equipment. In an advantageous embodiment, the ligand is firstly provided with a terminal cysteine residue for subsequent use in the coupling. The skilled person in this field also easily performs appropriate steps of purification.

In certain embodiments of the invention, the conditions for the adsorption step may be any conventionally used, appropriately adapted depending on the properties of the target antibody such as the pI thereof. The optional wash step can be performed using a buffer commonly used such as a PBS buffer.

The elution may be performed by using any suitable solution used for elution from Protein A media.

The present method is useful to capture target antibodies, such as a first step in a purification protocol of antibodies which are e.g. for therapeutic or diagnostic use. In one embodiment, at least 75% of the antibodies are recovered. In an advantageous embodiment, at least 80%, such as at least 90%, and preferably at least 95% of the antibodies are recovered using an eluent having a suitable pH for the particular ligand system. The present method may be followed by one or more additional steps, such as other chromatography steps. Thus, in a specific embodiment, more than about 98% of the antibodies are recovered.

As discussed earlier, for either SpA (domain E, D, A, B, C) or protein Z ligand, when at least one asparagine residue is mutated to an amino acid other than glutamine or aspartic acid, affinity media including these mutant ligands can better withstand cleaning procedures using alkaline agents (US patent application 2005/0143566). The increased stability means that the mutated protein's initial affinity for immunoglobulin is essentially retained for a prolonged period of time. Thus its binding capacity will decrease more slowly than that of the parental molecule in an alkaline environment. The environment can be defined as alkaline, meaning of an increased pH-value, for example above about 10, such as up to about 13 or 14, i.e. from 10-13 or 10-14, in general denoted alkaline conditions. Alternatively, the conditions can be defined by the concentration of NaOH, which can be up to about 1.0 M, such as 0.7 M or specifically about 0.5 M, accordingly within a range of 0.7-1.0 M.

Thus, the affinity to immunoglobulin i.e. the binding properties of the ligand, in the presence of the asparagine mutation as discussed, and hence the capacity of the matrix, is not essentially changed in time by treatment with an alkaline agent. Conventionally, for a cleaning in place treatment of an affinity separation matrix, the alkaline agent used is NaOH and the concentration thereof is up to 0.75 M, such as 0.5 M. Thus, its binding capacity will decrease to less than about 70%, preferably less than about 50% and more preferably less than about 30%, such as about 28%, after treatment with 0.5 M NaOH for 7.5 h.

In a further aspect, the present invention relates to a method of isolating an immunoglobulin, such as IgG, IgA and/or IgM, wherein a ligand or a matrix according to the invention is used. Thus, the invention encompasses a process of chromatography, wherein at least one target compound is separated from a liquid by adsorption to a ligand or matrix described above. The desired product can be the separated compound or the liquid. Thus, this aspect of the invention relates to affinity chromatography, which is a widely used and well-known separation technique. In brief, in a first step, a solution comprising the target compounds, preferably antibodies as mentioned above, is passed over a separation matrix under conditions allowing adsorption of the target compound to ligands present on said matrix. Such conditions are controlled e.g. by pH and/or salt concentration i.e. ionic strength in the solution. Care should be taken not to exceed the capacity of the matrix, i.e. the flow should be sufficiently slow to allow a satisfactory adsorption. In this step, other components of the solution will pass through in principle unimpeded. Optionally, the matrix is then washed, e.g. with an aqueous solution, in order to remove retained and/or loosely bound substances. The present matrix is most advantageously used with an intermediate washing step utilizing additives such as solvents, salts or detergents or mixture there of.

In a next step, a second solution denoted an eluent is passed over the matrix under conditions that provide desorption i.e. release of the target compound. Such conditions are commonly provided by a change of the pH, the salt concentration i.e. ionic strength, hydrophobicity etc. Various elution schemes are known, such as gradient elution and step-wise elution. Elution can also be provided by a second solution comprising a competitive substance, which will replace the desired antibody on the matrix. Regular protein A media based on native or recombinant protein A (e.g. MABSELECT™ and nProtein A SEPHAROSE™ 4 Fast Flow) normally elutes at pH 3.1-4.0 (measured at peak apex) mainly depending on its VH3 binding (see e.g. Ghose, S. et al. Biotechnology and Bioengineering 92 665-673 [2005]). The alkaline stabilized product MABSELECT SURE™, derived from the B-domain of protein A, essentially lacks the VH3 binding giving a higher elution pH: 3.7-4.0. For a general review of the principles of affinity chromatography, see e.g. Wilchek, M., and Chaiken, I. 2000. An overview of affinity chromatography. *Methods Mol. Biol.* 147: 1-6.

The substitution of the Asparagine residue at the position corresponding to N28 of B domain of Protein A or Protein Z unexpectedly increases the elution pH of immunoglobulins, or fusion proteins containing an Fc-fragment. The substitution thus provides a ligand which allows for elution above pH 4.0, preferably above 4.2, while the recovery yield is at least 80% or even >90% of that of the parental ligands. This results in gentler elution conditions which minimize the risk for aggregation or inactivation of the target protein.

Aggregate separation from monomers has been a challenge in antibody purification, especially at higher resolution. The present ligands provide an improved separation between monomers and aggregates, thus offer a viable approach for aggregate removal in the capture step, even at large scale.

EXAMPLES

Below, the present invention will be described by way of examples, which are provided for illustrative purposes only and accordingly are not to be construed as limiting the scope of the present invention as defined by the appended claims. All references given below and elsewhere in this application are hereby included herein by reference.

Mutagenesis of Protein

Site-directed mutagenesis was performed by a two-step PCR using oligonucleotides coding for the asparagine replacement. As template a plasmid containing a single domain of either Z or C was used. The PCR fragments were ligated into an *E. coli* expression vector (pGO). DNA sequencing was used to verify the correct sequence of inserted fragments.

To form multimers of Z(N28A) (SEQ ID NO.: 11) an Acc I site located in the starting codons (GTA GAC) of the C or Z domain was used, corresponding to amino acids VD. pGO Z(N28A)1 (SEQ ID NO.: 11) were digested with Acc I and CIP treated. Acc I sticky-ends primers were designed, specific for each variant, and two overlapping PCR products were generated from each template. The PCR products were purified and the concentration was estimated by comparing the PCR products on a 2% agarose gel. Equal amounts of the pair wise PCR products were hybridized (90° C.→25° C. in 45 min) in ligation buffer. The resulting product consists approximately to ¼ of fragments likely to be ligated into an Acc I site (correct PCR fragments and/or the digested vector). After ligation and trans-formation colonies were PCR screened to identify constructs containing Z(N28A)2 SEQ ID NO.: 3. Positive clones were verified by DNA sequencing.

Construct Expression and Purification

The constructs were expressed in the bacterial periplasm by fermentation of *E. coli* K12 in standard media. After fermentation the cells were heat-treated to release the periplasm content into the media. The constructs released into the medium were recovered by microfiltration with a membrane having a 0.2 µm pore size.

Each construct, now in the permeate from the filtration step, was purified by affinity. The permeate was loaded onto a chromatography medium containing immobilized IgG. The loaded product was washed with phosphate buffered saline and eluted by lowering the pH.

The elution pool was adjusted to a neutral pH and reduced by addition of dithio threitol. The sample was then loaded onto an anion exchanger. After a wash step the construct was eluted in a NaCl gradient to separate it from any contaminants. The elution pool was concentrated by ultra-filtration to 40-50 mg/ml.

The purified ligands were analyzed with LC-MS to determine the purity and to ascertain that the molecular weight corresponded to the expected (based on the amino acid sequence).

Activation

The base matrix used was rigid crosslinked agarose beads of 85 microns average diameter, prepared according to the methods of U.S. Pat. No. 6,602,990 and with a pore size corresponding to an inverse gel filtration chromatography Kav value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750. All buffers used in the experiments had been degassed by nitrogen gas for at least 5-10 min.

After immobilisation the gels were washed 3×GV with distilled water. The gels+1 GV {0.1 M phosphate/1 mM EDTA/10% thioglycerol pH 8.6} was mixed and the tubes were left in a shaking table at room temperature over night. The gels were then washed alternately with 3×GV {0.1 M TRIS/0.15 M NaCl pH 8.6} and 0.5 M HAc and then 8-10×GV with distilled water. Gel samples were sent to an external laboratory for amino acid analysis and the ligand content (mg/ml gel) was calculated from the total amino acid content.

Example 1

Prototype

Mutant Z(N28A)2 (SEQ ID NO: 3): ligand dimers containing two copies of protein Z, each containing the N28A substitution (Z(N28A)2), with ligand density of 6.6 mg/ml.
Z2 (similar to SEQ ID NO: 3, expect N28 is not substituted to A): ligand dimer containing two copies of protein Z (Z2), with ligand density of 5.9 mg/ml.
2 ml of resin packed in TRICORN™ 5 100 column.
Protein
Gammanorm 165 mg/ml (Octapharma), diluted to 1 mg/ml in Equilibration buffer.
Equilibration Buffer
APB Phosphate buffer 20 mM+0.15 M NaCl, pH 7.4 (Elsichrom AB)
Adsorption Buffer
APB Phosphate buffer 20 mM+0.15 M NaCl, pH 7.4 (Elsichrom AB).
Elution Buffers
Citrate buffer 0.1 M, pH 6.
Citrate buffer 0.1 M, pH 3.
CIP
0.1 M NaOH.
Experimental Details and Results:

The breakthrough capacity was determined with an ÄKTAExplorer 10 system at a residence time of 2.4 minutes. Equilibration buffer was run through the bypass column until a stable baseline was obtained. This was done prior to auto zeroing. Sample was applied to the column until a 100% UV signal was obtained. Then, equilibration buffer was applied again until a stable baseline was obtained.

Sample was loaded onto the column until a UV signal of 85% of maximum absorbance was reached. The column was then washed with equilibration buffer until a UV signal of 20% of maximum absorbance at flow rate 0.5 ml/min. The protein was eluted with a linear gradient over 10 column volumes starting at pH 6.0 and ending at pH 3.0 at a flow rate of 0.5 ml/min. Then the column was cleaned with 0.1M NaOH at flow rate 0.5 ml/min and re-equilibrated with equilibration buffer prior to cleaning with 20% ethanol. The last step was to check the sample concentration by loading sample through the bypass column until a 100% UV signal was obtained.

For calculation of breakthrough capacity at 10%, equation below was used. That is i.e. the amount of IgG that is loaded onto the column until the concentration of IgG in the column effluent is 10% of the IgG concentration in the feed.

$$q_{10\%} = \frac{C_0}{V_C}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;
$A_{sub}$=absorbance contribution from non-binding IgG subclass;
A(V)=absorbance at a given applied volume;
$V_c$=column volume;
$V_{app}$=volume applied until 10% breakthrough;
$V_{sys}$=system dead volume;
$C_0$=feed concentration.

The dynamic binding capacity (DBC) at 10% breakthrough was calculated and the appearance of the curve was studied. The curve was also studied regarding binding, elution and CIP peak. The dynamic binding capacity (DBC) was calculated for 5, 10 and 80% breakthrough. Some results are shown in Table 1. Similar capacity was observed for ligands with N28A substitution as compared to the parental N28 ligand (Z2).

IgG capacity and elution study for polyclonal human IgG were done on Z(N28A)2 and Z2. The capacity values did not differ between Z(N28A)2 and Z2. Some examples are shown in Table 1.

TABLE 1

Capacity data for Z(N28A)2 and Z2, using 1 mg/ml IgG dissolved in 20 mM PBS + 0.15M NaCl buffer, pH 7.4.

| prototype | Qb10 (mg/ml resin) | Qb80 (mg/ml resin) | Residence time (min) | Ligand density (mg/ml) |
|---|---|---|---|---|
| Z(N28A)2 | 32.0 | 47.4 | 2.4 | 6.6 |
| Z2 | 31.4 | 43.8 | 2.4 | 5.9 |

The elution studies were done for polyclonal human IgG in phosphate buffer. The elution pH increases significantly for Z(N28A)2 compared to Z2. A gradient elution from pH 6 to pH 3 was done using 0.1 M citrate buffers. The pH at peak apex was noted (see Table 2.)

TABLE 2

Elution pH for polyclonal human IgG.

| prototype | pH hIgG (first peak) | pH hIgG (second peak) |
|---|---|---|
| Z(N28A)2 | 4.41 | 3.96 |
| Z2 | 3.99 | 3.59 |

Note:
pH hIgG (first peak) and pH hIgG (second peak) are polyclonal IgG (Gammanorm).

Except for higher elution pH for the mutant ligands, they appear also to have better separation properties than Z2. Although there is tailing on both prototype ligands, with the mutant ligand there is an actual separation of the two peaks.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method of separating one or more immunoglobulin containing proteins from a liquid, the method comprising,
   (a) contacting the liquid with a separation matrix comprising ligands immobilised to a support, said ligands comprises one or more monomers having the sequence of SEQ. ID. NO. 2, wherein in at least one of the monomers, the Asparagine at the position N28 of SEQ. ID. NO. 2 has been substituted with another amino acid X to give a substituted monomer having a sequence of SEQ ID No.: 9;
   (b) allowing said immunoglobulin containing proteins to adsorb to the matrix by interaction with the ligands;
   (c) an optional step of washing the immunoglobulin containing protein adsorbed matrix; and
   (d) recovering said immunoglobulin containing proteins by contacting the matrix with an eluent which releases the proteins from the ligand at an elution pH that is higher than the elution pH when using a parental ligand that has the same sequence of said ligand except for said N28X substitution(s) under the same elution condition.

2. The method of claim 1, wherein the ligand comprises two or more copies of SEQ. ID. NO. 9.

3. The method of claim 1, wherein the ligand is multimeric and the other amino acid X is Glu, Leu, Gln, Trp, Lys, Asp, or Arg.

4. The method of claim 1, wherein the ligand is multimeric and each monomer has a sequence of SEQ ID NO.: 9 where the other amino acid X is Glu, Leu, Gln, Trp, Lys, Asp, or Arg.

5. The method of claim 1, wherein the protein is released at an elution pH that is at least 0.2 higher than when using the parental ligand under the same elution condition.

6. The method of claim 1, wherein the protein is released at an elution pH that is at least 0.4 higher than when using the parental ligand under the same elution condition.

7. The method of claim 1, wherein the protein is released at an elution pH of at least 4.0 with a recovery yield that is at least 80% of that of the parental ligand under the same elution condition.

8. The method of claim 1, wherein the ligands have affinity for the Fc part of an immunoglobulin but lack affinity for the Fab part of an immunoglobulin.

9. The method of claim 1, wherein the ligand is a dimer.

10. The method of claim 1, wherein the ligand is a tetramer.

11. The method of claim 1, wherein the immunoglobulin containing protein is a monoclonal antibody.

12. The method of claim 1, wherein the immunoglobulin containing protein is polyclonal antibody.

13. The method of claim 1, wherein the immunoglobulin containing protein is a fusion protein containing an immunoglobulin Fc portion fused with another protein.

14. The method of claim 1, wherein a pH gradient elution is performed in the recovery step which results in a more efficient separation of aggregate and monomer species of the immunoglobulin containing protein than using the parental ligand under the same elution condition.

15. The method of claim 1, wherein the protein is released at an elution pH of at least 4.2 with a recovery yield that is at least 80% of that of the parental ligand under the same elution condition.

16. The method of claim 1, wherein the protein is released at an elution pH of at least 4.0 with a recovery yield that is at least >90% of that of the parental ligand under the same elution condition.

17. The method of claim 1, wherein the protein is released at an elution pH of at least 4.2 with a recovery yield that is at least >95% of that of the parental ligand under the same elution condition.

18. The method of claim 1, wherein the ligand is a dimeric ligand comprising dimeric monomers having the sequence of SEQ. ID. NO. 10, wherein the Asparagine at the position N28 of SEQ ID NO.: 2 has been substituted with another amino acid X.

19. The method of claim 1, wherein the ligand is a dimeric ligand having a sequence of SEQ. ID. NO. 3.

20. A ligand comprising one or more monomers having the sequence of SEQ. ID. NO. 2, wherein in at least one of the monomers, the Asparagine at the position N28 of SEQ ID NO.: 2 has been substituted with another amino acid X to give a substituted monomer having a sequence of SEQ ID NO.: 9.

21. A matrix for affinity separation comprising multiple copies of the ligand of claim 20 coupled to a solid support.

22. The matrix of claim 21, wherein the solid support is polysaccharide based.

23. The matrix of claim 21, wherein the ligands are coupled via thioether bonds to the solid support.

24. The ligand of claim 20, wherein said ligand comprises two or more copies of SEQ. ID. NO. 9.

25. The ligand of claim 20, wherein said ligand comprises SEQ. ID. NO. 11.

26. The ligand of claim 20, wherein the ligand is multimeric and the other amino acid X is Glu, Leu, Gln, Trp, Lys, Asp, or Arg.

27. The ligand of claim 20, wherein the ligand is multimeric and each monomer has a sequence of SEQ ID NO.: 9 where the other amino acid X is Glu, Leu, Gln, Trp, Lys, Asp, or Arg.

28. The ligand of claim 20, wherein the ligands has affinity for the Fc part of an immunoglobulin but lack affinity for the Fab part of an immunoglobulin.

29. The ligand of claim 20, wherein the ligand is a dimer.

30. The ligand of claim 20, wherein the ligand is a tetramer.

31. The ligand of claim 20, wherein the ligand is a dimeric ligand having the sequence of SEQ. ID. NO. 10 where the other amino acid X is Ala, Glu, Leu, Gln, Trp, Lys, Asp, or Arg.

32. A dimeric ligand having the sequence of SEQ. ID. NO. 3.

* * * * *